US007311932B1

(12) United States Patent
Berggren et al.

(10) Patent No.: US 7,311,932 B1
(45) Date of Patent: Dec. 25, 2007

(54) COMPOSITION

(75) Inventors: Anna Berggren, Flyinge (SE); Marie Louise Johansson, Lund (SE); Kåre Larsson, Bjärred (SE); Anne-Marie Lindberg, Lund (SE); Jörgen Wiklander, Älta (SE)

(73) Assignee: Probi AB, Lund (SE)

( * ) Notice: Subject to any disclaimer, the term of this patent is extended or adjusted under 35 U.S.C. 154(b) by 0 days.

(21) Appl. No.: 09/926,586

(22) PCT Filed: May 22, 2000

(86) PCT No.: PCT/SE00/01024

§ 371 (c)(1), (2), (4) Date: Nov. 21, 2001

(87) PCT Pub. No.: WO00/70972

PCT Pub. Date: Nov. 30, 2000

(30) Foreign Application Priority Data

May 21, 1999 (SE) .................................. 9901856

(51) Int. Cl.
*A23L 1/29* (2006.01)
*A23L 2/00* (2006.01)

(52) U.S. Cl. ........................... 426/61; 426/72; 426/73; 426/74; 426/590; 426/810

(58) Field of Classification Search ................. 426/61, 426/72, 73, 74, 590, 810
See application file for complete search history.

(56) References Cited

U.S. PATENT DOCUMENTS

| | | | | |
|---|---|---|---|---|
| 5,902,743 | A * | 5/1999 | Luchansky et al. | 435/252.1 |
| 6,051,236 | A * | 4/2000 | Portman | 424/725 |
| 6,214,336 | B1 * | 4/2001 | Bukowska et al. | 424/93.45 |
| 6,599,504 | B1 * | 7/2003 | Wadstrom et al. | 424/93.45 |
| 6,835,376 | B1 * | 12/2004 | Neeser et al. | 424/93.45 |
| 2002/0090416 | A1 * | 7/2002 | Connolly | 426/2 |

FOREIGN PATENT DOCUMENTS

| | | |
|---|---|---|
| AU | 199737828 | 2/1998 |
| EP | 0856259 | 8/1996 |
| EP | 0916270 | 5/1999 |
| EP | 1020123 | 7/2000 |
| GB | 1157135 | 7/1969 |
| GB | 2335134 | 9/1999 |
| JP | 8280341 | 10/1996 |
| WO | 8908405 | 9/1989 |
| WO | 9406412 | 3/1994 |
| WO | 9846091 | 10/1998 |

OTHER PUBLICATIONS

Wedman, Recipe Source, Quick and Easy Diabetic Menus, http://www.recipesource.com/sid-dishes/beverages/00/re0005.html. copyright 1995-2000 SOAR.*

Yakuit's Sweet Success. 1930. http://216.109.117.135/search/chache?p=sports+and+lactobacilli+and+beverages+or+drinks.*

Tamine et al. Yoghurt science and Technology, 1985, Pergamon Press, New York, p. 242.*

Wilkes, A. Diet and Performance Beverages Respond to Increased Demands, Oct. 1992, Food product Design.com/archive/1992/1092DE.html.*

* cited by examiner

*Primary Examiner*—Helen Pratt
(74) *Attorney, Agent, or Firm*—Oblon, Spivak, McClelland, Maier & Neustadt, P.C.

(57) ABSTRACT

The invention describes a sports drink, which in addition to conventional additives contains viable lactobacilli having a positive effect on human intestinal mucosa. The sports drink preferably also contains micronutrients and proteins. The invention also refers to a tablet for the preparation of such a sports drink, containing viable freeze-dried lactobacilli in combination with micronutrients. In addition to providing liquid and nutrients replacement, the sports drink also relieves the stress symptoms, which are associated with long physical exercise.

12 Claims, No Drawings

COMPOSITION

CROSS-REFERENCE TO RELATED APPLICATIONS

The present application is a 371 application of PCT/SE00/01024, filed May 22, 2000.

The present invention refers to a sports drink which should be taken in connection with training and competition, especially in so-called endurance sports, such as skiing, marathon running and bicycling.

BACKGROUND OF THE INVENTION

It is generally known that physical exercise requires an increased and nutritionally adequate liquid intake. Dehydration rapidly decreases the capacity of an individual, but in hard training and competition the administration of salts and carbohydrates is also required in order to maintain the fluid balance, a proper salt balance and the energy level.

There is on the market today a large number of fluid and/or energy providing beverages. So called sports drinks are normally intended to be taken directly during the physical exercise to meet with the loss of fluids and salts of the body. A sports drink can be hypotonic, that is have a lower content of salts and sugars than the human body fluid, which means that it is quickly taken up by the body. Such a beverage is well fitted for short training sessions. An isotonic sports drink, that is having about the same concentration of salts and sugars as the human body, may well be used during harder and longer training sessions. A conventional sports drink contains in addition to water, carbohydrates, such as different sugars, in an amount of 4-8%, salts and minerals.

There are also different types of nutritional additives based on vitamins, minerals and other antioxidants, or in other ways stimulating substances such as caffeine or ginseng, which can either be provided in a sports drink or in the shape of tablets or powder or any other conventional form such as an energy cake.

In connection with physical exercise it is now generally believed that there is also an increased demand of proteins and many nutritional additive products therefore also contains one or more amino acids or proteins. This is especially true for products, which are used by body-builders and other strength sports performers.

When practising an endurance sport or exercising physically during a long period of time the body will be in a state of stress. This implies an increased flow of blood to the muscles, increased production of free radicals, and increased level of the so called stress hormones adrenaline, noradrenaline and cortisol. This state of stress also leads to gastrointestinal problems for many people practising said sports, such as marathon runners and hard training athletes. The gastrointestinal problems can be manifested in many different ways, such as constipation, diarrhea, stomach ache, cramp or nausea (Nancy Rehrer et al., Gastrointestinal complaints in relation to dietary intake in triathletes, International Journal of Sport Nutrition, 1992, 2, 48-59). Competitive long-distance running is also said to induce gastrointestinal blood loss which may contribute to iron deficiency, runner's anaemia (James G. Stewart et al., Gastrointestinal Blood Loss and Anaemia in Runners, Annals of Internal Medicine, 1984, Vol. 100, No. 6, 843-845). Said intestinal bleedings might be due to a weakened intestinal mucosa.

PRIOR ART

GB 2 335 134 A, Stalplex Ltd, discloses a carbonated sport beverage comprising fruit juice, carbohydrates and a soluble whey protein hydrolysate. The beverage is to be used by people engaged in physical activities. Nothing is, however, stated about the optional effects of the beverage.

WO 89/08405, Nils Molin et al., describes a nutrient composition for administration to patients in feeding by tube or for use as a health drink. The nutrient composition comprises fermented oat-flour in combination with lactobacilli, optionally also soya flour or skim milk powder and supplementary mineral substances and vitamins. A nutrient composition should cover the total nutrient requirements and should contain carbohydrates, proteins and fat. The amount of antioxidants will on the other hand be fairly low.

There is therefore still a need for an improved sports drink which can alleviate the symptoms of prolonged physical activity.

DESCRIPTION OF THE INVENTION

The purpose of the invention is to provide a sports drink which in addition to a nutrient and fluid supplementation before or after physical activity in order to build up and recover, respectively, the energy and fluid levels of the body, also relieves the symptoms of stress. It has now surprisingly been shown that viable lactobacilli can be mixed with micro-nutrients, carbohydrates, salts and proteins, without negative effects on e.g. antioxidants, to a beverage having a good taste and a good shelf-life.

The invention refers to a sports drink which is characterised in containing viable lactobacilli having a positive effect on human intestinal mucosa.

The invention especially refers to a sports drink which comprises micronutrients in combination with conventional additives for a sports drinks, which is characterised in that it also contains viable lactobacilli having a positive effect on human intestinal mucosa.

Lactobacilli which are suitable to use in accordance with the invention comprise those different strains of different species which have a positive effect on human intestinal mucosa. Such an effect involves an ability to colonise in the intestines and thereby protect the intestinal mucosa, for instance by initiating the production of mucin or short chain fatty acids. Examples of strains having this ability can be found among the following species *Lactobacillus acidophilus, Lactobacillus casei, Lactobacillus fermentum, Lactobacillus paracasei, Lactobacillus plantarum, Lactobacillus reuteri, Lactobacillus rhamnosus.*

A suitable species of *Lactobacillus*, which can be used according to the invention, is a *Lactobacillus plantarum* being able to adhere to the intestinal epithet and colonise in the intestines. Particularly suitable strains of this species comprise a mannose specific adhesin, such as described in WO 96/29083, and are part of a cluster of *L. plantarum* having more than 70% similarity to *L. plantarum* 299, deposited on Jul. 2, 1991 at Deutsche Sammlung von Mikroorganismen und Zellkulturen GmbH, Braunschweig, Germany under the accession number DSM 6595, with respect to REA, that is restriction enzyme analysis of the total chromosomal DNA. A preferred strain is *L. plantarum* 299v, deposited on Mar. 16, 1995 under the accession number DSM 9843.

Other strains of interest which can be used in a sports drink according to the invention are the probiotic strains *Lactobacillus rhamnosus* 271 (DSM 6594), *Lactobacillus*

*rhamnosus* GG (ATCC 53103), *Lactobacillus casei rhamnosus* LB 21, *Lactobacillus casei* Shirota, *Lactobacillus johnsonii* Lj1, and *Lactococcus lactis* L1A.

Micronutrients in this context refers to vitamins, minerals and other additives having an antioxidising or stimulating effect. As examples can be mentioned:

Ascorbic acid or vitamin C, which acts as an antioxidant but also takes part in hydroxylation reactions. Lack of ascorbic acid can result in such symptoms as tiredness, weakness and also loosening of the teeth. According to the Swedish nutritional recommendations the intake should be 35-60 mg per day;

Carotenoids acts as antioxidants. The carotenoid group includes both carotenes and xantophylles. The difference between them is the occurrence of oxygen in the xanthophyll molecule. Examples of carotenoids are a-carotene, β-carotene, γ-carotene, lycopene, lutein, chryptoxanthin, astaxanthin, canthaxanthin, and zeaxanthin. About 50 of approximately 500 naturally occurring carotenoids are precursors of retinol. E.g. β-carotene is a provitamin to vitamin A. The vitamin is needed for the sight, growth, reproduction and the normal differentiating and stability of the epithet tissues. A-vitamin is also considered to be of importance for the immune defence. The recommended daily intake of retinol equivalents for men is 1000 μg and for women 800 μg per day. Astaxanthin is a powerful antioxidant, which has proven to give an increased antibody production;

Vitamin E, natural or synthetic, is considered to function as an antioxidant and by that contribute to the stability of the cell membranes by protecting the polyunsaturated fatty acids in the lipids of the membranes. The recommended daily intake is 10 mg α-tocopherol equivalents for men and 8 mg for women;

Vitamin B6 is the common name for pyridoxine, pyridoxal and pyridoxamine. Lack of vitamin B6 is uncommon and in that case occurs together with lack of other B-vitamins. Symptoms are for instance cramps and anemia. The recommended intake is 1.5-2 mg per day and the need is proportional to the amount of protein, which is metabolized in the body;

Thiamin, vitamin B1, acts as a coenzyme in several enzymes of importance for the energy metabolism in e.g. the citric acid cycle. A lack thereof can cause beriberi, which involves disorders of the nerve system, heart and digestion organs. An intake of 0.5 mg per 1000 kcal is believed to give tissue saturation, the recommendations are 1 mg and above;

Riboflavin, vitamin B2, takes part in the conversion of tryptophane into niacin. A lack thereof is generally connected to a deficiency of other B-vitamins and symptoms of this deficiency can be hypersensitivity to light and reddening mouth mucosa. Recommended intake is 1.6 mg per day for men and 1.3 mg for women;

Niacin, nicotinic acid, is a part of coenzymes and constitutes a part of NAD and NADP, which are necessary in the conversion of glucose, amino acids and fat. Lack thereof can result in pellagra. Characteristics are changes in the skin, gastro-intestinal system. Recommended intake of niacin should be proportional to the consumption of energy and is about 13-18 mg per day;

Cobalamin, vitamin B12, acts as a coenzyme in transferring one-carbon groups and takes part, together with folic acid, in the formation of active methyl groups. Vitamin B12 deficiency can result in pernicious anaemia and also cause nerve damages. According to Swedish nutritional recommendations 3 μg per day is regarded to cover the requirement;

Folacin, folic acid, acts as a coenzyme and transfers one-carbon fragments in amino acid synthesis and nucleic acid synthesis. Folacin deficiency results in impaired cell division, disordered protein conversion and megaloblastic anaemia. Recommended intake of folacin is 200 μg per day;

COQ10 or coenzyme Q10 is an antioxidant protecting against free radicals, in particular oxidation of lipids is prevented. In general about 100 mg per day is given;

Flavonoides, which are present in vegetable food, are powerful polyphenolic antioxidants preventing oxidation of lipoproteins and reducing the risk of coronary heart diseases;

Copper is part of enzymes, which are necessary for the energy metalbolism of the cells, synthesis of connective tissue, synthesis of neuropeptides and in the body defence against free radicals. Deficiency symptoms in adults are dysarrhytmia and other changes of the heart function. Recommended intake is 1.2 mg for adults;

Magnesium is the prosthetic group of many enzymes and also functions as an activator. ATP:ase is for instance magnesium dependent and is part of inter alia the contraction of the muscle cells, the Na/K-pump. Magnesium is also needed for nucleic acid and protein synthesis. In addition, the function of certain nerve cells depends on magnesium. Recommended intake of magnesium is 280 mg per day for women and 350 mg for men;

Manganese inter alia takes part of the synthesis of proteins, mucopolysaccharides and cholesterol. Possible symptoms of manganese deficiency in man are changes of the skin and hypocholesterolemia. Recommended intake is 25 mg per day;

Selenium mainly is part of the enzyme glutathioneperoxidase and protects the cells from oxidative lesions. The recommended intake of selenium is 40 μg for women and 50 μg for men. The intake should not exceed 5 μg per kg body weight and day. Selenium deficiency can cause a heart-muscle disease;

Zinc is a part of many enzymes. Zinc deficiency can be manifested as growth retardation and changes of the skin. Recommended intake of zinc according to the Nordic nutritional recommendations is 7 mg for women and 9 mg for men. Too high an intake negatively effects the metabolism of other trace elements. The zinc intake should not exceed 45 mg for adults and 25 mg for children;

Chromium is the biological active component of the glucose tolerance factor, which potentiates the insulin activity. A supplement of chromium could improve the efficiency of insulin.

The invention especially refers to a sports drink containing micronutrients selected from the group consisting of ascorbic acid, vitamin E, carotenoids, pyridoxine, thiamine, riboflavine, niacin, cobalamine, folacin, Q10, flavonoides, copper, magnesium, manganese, selenium, zinc, and chromium. A synergistic effect can be expected for a mixture of the stated compounds. It is for instance well known that vitamin C, vitamin E and selenium have a synergistic effect.

Salts of sodium and potassium are necessary to administer after exercise in order to recover the salt balance; this is true especially in a warm climate with attendant perspiration. Acute salt deficiency causes nausea and impaired nerve impulses, which inter alia is manifested in a swaying and stumbling gait. Moderately high levels of sodium, such as up to 50-60 mmol/l, and also some potassium should therefore be part of the composition according to the invention in order to compensate for losses through perspiration.

A preferred combination of micronutrients and salts in a sports drink according to the invention is, per 1000 g sports drink:

| | |
|---|---|
| ascorbic acid | 500-1200 mg |
| vitamin E | 250-375 mg |
| β-carotene | 15-25 mg |
| pyridoxine | 15-25 mg |
| sodium | 20-60 mg |
| potassium | 60-100 mg |
| copper | 0.5-1.5 mg |
| magnesium | 120-175 mg |
| manganese | 1-3 mg |
| selenium | 0.05-0.15 mg |
| zinc | 5-15 mg |

According to a preferred aspect the invention refers to a sports drink, which in addition to micronutrients and live lactobacilli also comprises proteins.

Proteins, which are suitable to use in a sports drink according to the invention, should be water soluble, acid stable and heat stable. As examples can be mentioned different milk proteins, especially whey proteins or whey protein hydrolysates. Whey protein isolates are one of the protein sources supplying most essential amino acids and branched amino acids per g of nitrogen. A preferred whey protein is highly soluble in water and forms low viscous, homogenous and comparatively clear solutions after mixing with water. Another possible source of proteins is bovine colostrum. Different amino acids, especially branched amino acids which are taken up by the muscles, can also be added to give a corresponding supplement of energy. Essential, branched amino acids, which can be added with the whey protein, are leucine, isoleucine and valine.

The sports drink of the invention also contains carbohydrates and salts in an aqueous solution, preferably flavoured with a fruit juice concentrate and aromas.

Preferred carbohydrates are the so-called slow carbohydrates, having a low glycemic index. GI, glycemic index, is a measure of how quickly the carbohydrates of a food enter the blood. Fructose is the monosaccharide having the lowest glycemic index and is particularly preferred. If you wish to prepare a beverage which is hypotonic it could, however, be adequate to use a so called polysugar, maltodextrin, which has a high carbohydrate concentration but a low osmotic pressure, in an amount of 2-20 dextrose equivalents. For different reasons it might, however, be preferred to use the slow carbohydrate in admixture with a carbohydrate having a high glycemic index, for instance other mono- or disaccharides, such as glucose and saccharose.

If the monosaccharide content is lower than 50 g per 1000 g, an isotonic beverage is obtained; at higher contents a hypotonic beverage. If this beverage also contains salt the amount will be different.

Aromas can for instance be produced from different concentrated fruit juices and is preferably used when the sport drinks contain proteins, especially whey proteins, which might otherwise give the beverage a special, bitter taste.

A sports drink according to the invention can for instance per 1000 g contain:

| | |
|---|---|
| whey protein | 15-60 g |
| carbohydrates | 40-150 g |
| micronutrients | 1-2 g |
| probiotic strain of *Lactobacillus* | $5 \cdot 10^7$-$5 \cdot 10^8$ cfu/ml |

According to a preferred aspect of the invention the sports drink contains per 1000 g:

| | |
|---|---|
| whey protein isolate | 15-60 g |
| mono- and disaccharides | 40-150 g |
| micronutrients | 1-2 g |
| *L. plantarum* DSM 9843 | $5 \cdot 10^7$-$5 \cdot 10^8$ cfu/ml |

According to another aspect the invention refers to a nutritional additive comprising micronutrients in combination with freeze-dried, viable lactobacilli, especially in the shape of a tablet or a powder. This nutritional additive can also be an energy cake or some other conventional nutritional product wherein the lactobacilli can be preserved alive.

The invention especially refers to a tablet for preparing of a sports drink as above, which tablet comprises micronutrients in combination with freeze-dried, viable lactobacilli. Such a tablet can be prepared by mixing a freeze-dried culture, in an amount of 10-20 W by weight of the total composition, of selected lactobacilli with micronutrients, 1-3%, and an adequate tablet making material which allows for the use of a comparatively low punching pressure at the tabletting, for instance according to the process which is described in WO 97/07822. By using a reduced punching pressure it will be possible to maintain 90-95% of the viability of the bacteria. Possible tablet making materials are poly- and oligosaccharides, especially based on fructose, calcium diphosphate, micro-crystalline cellulose and maltodextrine as a filler, xanthan as a slime forming agent and magnesium stearate as a lubricant. The tablet can also be an effervescent.

By mixing a tablet prepared in this way with water or with water and carbohydrates, with or without proteins and salts, or with a conventional sports drink, a sports drink according to the invention for direct consumption is obtained. It is of course also possible to make the mixture in vivo, that is to eat the tablet in connection with the intake of the fluid.

A hypertonic sports drink according to the invention containing proteins, carbohydrates and lactobacilli can preferably be taken before or after competition or training in an amount of ½ M to 1 liter per day. This corresponds to a total daily consumption of $3 \cdot 10^{10}$-$5 \cdot 10^{10}$ cfu/ml. The beverage is, owing to its content of proteins and lactobacilli, less apted for being taken during the physical exercise. There is, however, nothing that prevents the use of a beverage consisting of hypertonic amounts of carbohydrates and salts and micronutrients in combination with lactobacilli and optimal flavouring additives also during the physical exercise as such.

The invention in addition refers to the use of lactobacilli for the preparation of a sports drink to be used to prevent and treat stress symptoms, disturbances of the gastrointestinal tract, and lesions of the mucose membrane of the intestines. It has been shown that a regular intake of a sports drink according to the invention has a positive effect on the stress related gastrointestinal problems. By taking this beverage the negative effect of stress is reduced, the risks of disorders in stomach and intestines are decreased and, especially, the risk of disorders of the intestinal mucosa is reduced.

It is probable that the most favorable effect on the intestinal mucosa is obtained with a sports drink containing a combination of whey protein, micronutrients and lactobacilli.

EXAMPLES

Example 1

Hypertonic Sports Drink

For the preparation of a hypertonic sports drinks the following constituents are used

| | |
|---|---|
| whey proteins | 22.5 g |
| fructose | 20 g |
| glucose | 60 g |
| saccharose | 40 g |
| oatbase | 50 g |
| micronutrients | 1.5 g |
| fruit juice concentrate | 15 g |
| aromas | 1.5 g |
| water | q. s. ad 1000 g |
| citric acid for adjusting pH to 3.4 | |

All the constituents are weighed. The whey protein, Lacprodan® DI-9213 (MD-Foods, Viby, Denmark), is mixed with water and then homogenised on ultraturrax, position 2 (13,000 rpm), for about 1 minute. Then fructose, glucose and saccharose, and aromas are added, mixed and heated during stirring to 90° C. for 5 minutes in a water-bath. The fruit juice concentrate could be from lemon-lime, black current or tropical, all from Skånemejerier Ekonomisk förening, Malmö. The aroma has a lemon-lime taste and has been obtained from Quest International, Lund. The batch is then cooled to room temperature and the oatbase which contains *Lactobacillus plantarum* 299v in an amount of $1–2 \cdot 10^9$ cfu per ml, and micronutrients are added. After mixing a well tasting beverage is obtained which is aseptically packed and then cool stored.

The micronutrients and the proportion between them are, calculated on the metal when applicable, as follows

| | |
|---|---|
| ascorbic acid | 800 mg |
| vitamin E | 320 mg (400 IE) |
| β-carotene | 20 mg |
| pyridoxine | 20 mg |
| copper ($CuSO_4$) | 1 mg |
| magnesium (MgO) | 150 mg |
| manganese ($Mn_2SO_4$) | 2 mg |
| selenium ($Na_2SeO_3$) | 100 µg |
| zinc ($ZnSO_4$) | 10 mg |

and constitutes a powder mixture.

The oatbase used above is a storage solution of lactobacilli and is prepared from oat meal, malt flour and water which are mixed and heated at different temperature ranges to give a proper substrate for the selected strain of *Lactobacillus*. In this case *Lactobacillus plantarum* DSM 9843 is used, which is added to the cooled oats mixture and which after fermentation gives a content of about $2 \cdot 10^9$ cfu/ml oatbase.

The sports drink thus prepared contains per 100 g

| | |
|---|---|
| protein | 2.1 g |
| fat | 0.1 g |
| carbohydrates | 13 g |
| sodium | 2.3 mg |
| potassium | 6.4 mg |
| lactobacilli | $5 \cdot 10^7$ cfu/ml |

The shelf-life of the prepared sports drink has turned out to be at least 4 weeks when stored in a refrigerator, +4 to +8° C.

Example 2

Hypertonic Sports Drink

For the preparation of another hypertonic sports drinks the following constituents are used

| | |
|---|---|
| Lacprodan ® DI-9213 | 45 g |
| fructose | 120 g |
| oatbase | 50 g |
| micronutrients | 1.5 g |
| fruit juice concentrate | 20 g |
| aromas | 1.5 g |
| water | q. s. ad 1000 g |

The same procedure as described in Example 1 was followed, the same micronutrients and lactobacilli were added and the sports drink thus prepared contained per 100 g

| | |
|---|---|
| protein | 4 g |
| fat | 0.1 g |
| carbohydrates | 13 g |
| sodium | 4.5 mg |
| potassium | 8.6 mg |
| lactobacilli | $5 \cdot 10^7$ cfu/ml |

Example 3

Tablet

The following ingredients are mixed in the stated weight proportion

| | |
|---|---|
| *L. plantarum* DSM 9843, freeze-dried | 20% |
| inulin | 78% |
| micronutrients | 2% |

and compressed into tablets. The micronutrients have the composition stated in Example 1 above. 1 tablet could preferably be taken together with about ½ liter of fluid.

Example 4

Table

In the same way as in Example 3 the following ingredients are mixed, giving a tablet having improved solubility properties.

| | |
|---|---|
| *L. plantarum* DSM 9843, freeze-dried | 10% |
| inulin | 85% |
| micronutrients | 2% |
| magnesium stearate | 1% |
| xanthan | 2% |

Biological Tests

Effects of *L. plantarum* DSM 9843 in a Rat Intestinal Bleeding Model 36 male Sprague-Dawley rats were used for the experiment. They were housed in separate metabolic cages to collect stool individually for evaluation. The animals were kept at room temperature, 22° C., with a controlled 12 h light/dark cycle and had free access to standard rat chow and drinking water. There were three different experimental groups with 12 rats in each. Group 1 was the negative control which received no treatment. Group 2 was the positive control which was given DSS, dextrane sulphate, in order to induce intestinal bleeding. The rats in Group 3 were treated with DSS+*L. plantarum* DSM 9843. All rats underwent sham operation for insertion of a pump for a later experiment under anaesthesia. On day 1 the rats were operated and on the following 6 days DSS was administered. Group 1 had free access to tap water and Groups 2 and 3 received ad libitum 5% (w/v) DSS (ICN Biomedicals Inc. Aurora, Ohio, USA) dissolved in the drinking water. The Group 3 rats were fed enterally with an oatmeal drink containing $1\times10^{10}$ cfu/ml of *L. plantarum* DSM 9843 twice daily in a volume of 2 ml through an oro-gastric tube.

The following results were obtained

TABLE 1

Mean of Disease Activity Index

| day | Group 1 | Group 2 | Group 3 |
|---|---|---|---|
| 1 | 0.3 | 0.4 | 0.2 |
| 2 | 0.1 | 0.5 | 0.6 |
| 3 | 0.0 | 0.5 | 0.5 |
| 4 | 0.0 | 0.8 | 0.9 |
| 5 | 0.1 | 1.5 | 1.0* |
| 6 | 0.2 | 2.3 | 1.8* |
| 7 | 0.0 | 2.8 | 2.3* |

*denotes P < 0.05 compared to Group 2, that is the DSS group

The Disease Activity Index, which is a combination of scores for weight loss, stool consistency and bleeding, divided by 3, was scored as below

TABLE 2

Scoring of Disease Activity Index

| Score | Weight loss, % | Stool consistency | Bleeding |
|---|---|---|---|
| 0 | none | normal = well-formed pellets | negative |
| 1 | 1-5 | | |
| 2 | 5-10 | loose stool = pasty, not sticking to the anus | hemoccult + |
| 3 | 10-20 | | |
| 4 | >20 | diarrhea = liquid stool sticking to the anus | gross bleeding |

The results of this test show that administration of *Lactobacillus plantarum* to the intestines has a positive effect on the intestinal mucosa.

Pilot Study with the Sports Drink of Example 1

7 hard training persons, No. 1-7, were given the sports drink according to Example 1 and were told to take % to 1 liter per day before or after the physical exercise for a period of 4 weeks. They were also asked to give their views on optional differences as to gastrointestinal behaviour, recovery, sense of well-being, ache after training and optional other aspects.

Person No. 1 is a long-distance runner training more than 7 times a week. He experienced no gastrointestinal problems during the test. From day 5 he finds that his capacity and total well-being had increased. After 28 d the ache after training has decreased.

Person No. 2 is a handball player, and mentions less ache after training and increased well-being.

Person No. 3 is an athlete. In addition to an increased well-being she believes that the recovery is quicker and sometimes the performance better.

Person No. 4 is a marathon runner. He liked the drink and found it of value during hard training, but finds the test period of 4 weeks to be too short. He had rarely any gastrointestinal problems—only during extremely intensive training sessions.

Person No. 5 is a marathon runner who mentions less ache after training, increased well-being and good recovery. Above all she is happy with an improved gastrointestinal behaviour, previous diarrhea after hard training has disappeared and she has no longer any gastrointestinal problems.

Person No. 6 is an athlete, running 400 and 800 m. She found the drink to increase her well-being, reduce the ache after training, reduce the disease frequence, increase the recovery rate.

Person No. 7 is an athlete, running middle distances. She experienced an improved gastrointestinal behaviour, an increased recovery rate, a reduced infection frequency and in general an improved total well-being.

The conclusions from this pilot study are that those individuals who had gastrointestinal problems in connection with hard training experienced an clear improvement; the reduction of the ache after training was also a common feature.

Studies in Progress

In order to closer investigate the effects of the sports drink of the invention different tests are to be performed. In one study different parameters, such as antioxidative capacity in blood, gastrointestinal function and optional effects on the microflora, are to be studied on healthy persons having a high tempo in their working life. Another study is to be made with hard training athletes, in which maximum oxygen uptake, lactate treshold values, anaerobic capacity and power of endurance are to be tested.

In connection with a marathon competition the runners will be asked to participate in a study to evaluate the effects of the sports drink of the invention in reducing the occurrence of faecal blood.

The invention claimed is:

1. A sports drink comprising per 1000 g 500-1200 mg ascorbic acid, 250-375 mg vitamin E, 15-25 mg pyridoxine, 0.5-1.5 mg copper, 120-175 mg magnesium, 1-3 mg manganese, 0.05-0.15 mg selenium, 5-15 mg zinc, 20-60 mg sodium, 60-100 mg potassium, 15-25 mg β-carotene, and one or more micronutrients selected from the group consisting of carotenoids, thiamine, riboflavin, niacin, cobalamin, folacin, Q10, flavonoids, and chromium in combination with additives for sports drinks, and viable lactobacilli selected from the group consisting of *Lactobacillus paracasei, Lactobacillus rhamnosus*, and *Lactobacillus plantarum* 299v (DSM 9843) and which have a positive effect on human intestinal mucosa.

2. A sports drink according to claim 1, which comprises proteins, optionally in combination with amino acids.

3. A sports drink according to claim 2, wherein the protein is a whey protein or whey protein hydrosylate.

4. A sports drink according to claim 1, which comprises carbohydrates having a low glycemic index, optionally in combination with carbohydrates of a high glycemic index.

5. A sports drink according to claim 1, comprising per 1000 g

| | |
|---|---|
| whey proteins | 15-60 g |
| carbohydrates | 40-150 g |
| micronutrients | 1-2 g |
| *Lactobacillus paracasei*, *Lactobacillus plantarum* or *Lactobacillus rhamnosus* | $5 \cdot 10^7$-$5 \cdot 10^8$ cfu/ml. |

6. A sports drink according to claim 1, comprising per 1000 g:

| | |
|---|---|
| whey protein isolate | 15-60 g |
| mono- and disaccharides | 40-150 g |
| micronutrients | 1-2 g |
| *Lactobacillus paracasei*, *Lactobacillus plantarum* or *Lactobacillus rhamnosus* | $5 \cdot 10^7$-$5 \cdot 10^8$ cfu/ml. |

7. A tablet for the preparation of a sports drink according to claim 1 in vivo or in vitro, comprising micronutrients in combination with freeze-dried, viable lactobacilli selected from the group consisting of *Lactobacillus paracasei, Lactobacillus plantarum* and *Lactobacillus rhamnosus.*

8. A method of treating stress symptoms, gastrointestinal disturbances, and lesions of the mucosal membrane of the intestines in an individual in need thereof, comprising providing the sports drink according to claim 1 to the individual wherein the sports drink is ingested by the individual in an amount sufficient to treat stress symptoms, gastrointestinal disturbances and lesions of the mucosal membrane.

9. A sports drink according to claim 2, which comprises carbohydrates having a low glycemic index, optionally in combination with carbohydrates of a high glycemic index.

10. The sports drink according to claim 1, wherein the viable lactobacilli are *Lactobacillus plantarum* 299v.

11. The sports drink according to claim 1, wherein the viable lactobacilli are *Lactobacillus paracasei.*

12. The sports drink according to claim 1, wherein the viable lactobacilli are *Lactobacillus rhamnosus.*

* * * * *